United States Patent [19]

Hahn et al.

[11] 4,223,070

[45] Sep. 16, 1980

[54] IMPREGNATED POROUS GRANULES WITH SLOW RELEASE PORE MEMBRANES AND PROCESS THEREFOR

[75] Inventors: Alice U. Hahn, Orinda; Richard H. Rider, El Cerrito; Herbert B. Scher, Moraga; Garrard L. Hargrove, Vacaville, all of Calif.

[73] Assignee: Stauffer Chemical Company, Westport, Conn.

[21] Appl. No.: 902,572

[22] Filed: May 4, 1978

[51] Int. Cl.$^2$ .................. B32B 19/00; C08J 5/24; C08J 9/40; C08K 7/24
[52] U.S. Cl. .................. 428/407; 427/215; 427/220; 428/905; 428/907; 427/221
[58] Field of Search ........... 428/407, 423, 424, 454, 428/306, 307, 543, 538, 403, 404, 905, 907; 427/212, 215, 220, 221; 71/64 F, DIG. 1

[56] References Cited

U.S. PATENT DOCUMENTS

| 3,223,518 | 12/1965 | Hansen | 427/212X |
| 3,821,135 | 6/1974 | King | 428/306 |
| 4,119,565 | 10/1978 | Baatz et al. | 71/64 F X |
| 4,140,516 | 2/1979 | Scher | 71/64 F X |

FOREIGN PATENT DOCUMENTS 1091077 11/1967 United Kingdom .

OTHER PUBLICATIONS

Cardarelli, Chem. Tech., Aug. 1975, pp. 482+.

*Primary Examiner*—William J. Van Balen
*Attorney, Agent, or Firm*—M. Henry Heines

[57] ABSTRACT

Open-ended pores of a porous granule are filled with a liquid material which is at least partially immiscible with water, and sealed with a porous polyurea membrane which limits the release rate of the material into the surrounding medium. The membrane is formed by (a) applying to the bare granule an organic solution comprising the liquid material and an organic polyisocyanate, followed by (b) applying to the granule an aqueous solution comprising water and a catalytic amount of a catalyst selected from the group consisting of a basic organic tertiary amine and an alkyl tin carboxylate.

28 Claims, No Drawings

IMPREGNATED POROUS GRANULES WITH SLOW RELEASE PORE MEMBRANES AND PROCESS THEREFOR

BACKGROUND OF THE INVENTION

This invention relates to coated granules. In particular, this invention relates to porous granules containing liquid material held therein for slow release by a porous coating covering the opening of each pore. The invention further relates to a process for preparing such coated granules. The effect of the coating is to delay the rate of release of the liquid material to the surrounding medium. The coating thus serves to increase the useful life of the granules as a means for dispersing the material into the surrounding medium. By limiting the maximum rate of diffusion from the pores, the coating also helps to prevent the usual occurrence of a rapid initial increase and subsequent rapid decrease in the concentration of the material in the surrounding medium. A flatter curve of concentration vs. time outside the granule is thus achieved.

The use of membranes, coatings, and capsules for the controlled release of liquid materials is well known in the art of both agricultural and non-agricultural chemicals. In the agricultural area, such slow release techniques have helped improve the efficiency of herbicides, insecticides, fungicides, bactericides, and fertilizers. Coating technology in the agricultural area is manifest in the form of coated droplets, such as microcapsules, coated solids such as porous or non-porous particles, and coated aggregates of solid particles. Non-agricultural uses include encapsulated dyes, inks, pharmaceuticals, flavoring agents, and fragrances. In some instances, a water soluble encapsulating material is desired, whereby the encapsulated material is immediately released upon contact of the capsule with water. Some coatings are designed to release the entrapped liquid upon the application of external pressure to break or crush the coating.

The above coatings completely enclose the material held inside, and prevent any release of the material until the coating is broken, dissolved, or otherwise removed. Other coatings are porous in structure, permitting a slow rate of diffusion of the entrapped material to the surrounding medium. This type is particularly effective in the agricultural area. Water insoluble coatings are particularly useful in agriculture, especially when the surrounding medium is water itself, a water-containing material such as soil, or air in areas of frequent rainfall.

Porous granules offer distinct advantages for chemicals in a wide variety of commercial applications by improving the ease of handling as well as the ease of distributing or dispersing the chemicals over a wide area, and by offering slow release characteristics inherent in the porous structure of the granule itself. In addition, granules of high pore volume are capable of retaining a considerable volume of liquid inside their pores, with only a small fraction initially exposed to the outer medium.

The use of coatings of the external granule surface to further enhance the release delaying characteristics of the granules is known. Certain problems are encountered when conventional techniques are used, however. Adhesion of the coating to the surface of the granule is often a problem. Adhesion can be improved by pretreatment of the uncoated granule surface. Alternatively, an initial primer coating can be applied. Since the primer coating itself is unsatisfactory for slow release purposes, an outer encapsulating coating must then be applied.

An additional problem encountered with conventional techniques of coating granules is achieving a uniform coating thickness. When the coating material is sprayed onto the granule, much of the material lands on the bare granule surface while only some of it lands in the pore containing the pesticide or other liquid whose delayed release is desired. The thickness of the coating varies according to the spraying technique used and the angle at which the spray strikes the granule. Some of the coating material will be wasted on the dry granule surface where it has no slow release effect. Some areas of exposure of the liquid contained in the granule pores will be coated very lightly, allowing too much liquid to escape. Other important areas may not be coated at all. This lack of uniformity arises in part from the fact that the coating composition is not premixed with the pesticide in a single body of liquid prior to its application to the granule. The efficiency of the coating material thus applied and the reproducibility of the process are less than desired.

It is therefore an object of this invention to overcome the problems stated above and provide a process for the preparation of porous granules impregnated with a liquid material and sealed with an encapsulating coating which uniformly seals the liquid material inside the pores and provides a controlled rate of release.

Another object of this invention is to provide a novel impregnated granule with pores uniformly sealed by a single uniform coating capable of providing a controlled rate of release of the liquid contained in the pores.

SUMMARY AND BRIEF DESCRIPTION OF THE INVENTION

According to the present invention, it has been discovered that open-ended pores of a porous granule can be efficiently and uniformly sealed with a porous polyurea membrane, entrapping therein a liquid material and allowing said material to diffuse therethrough at a slow rate. In particular, this invention relates to a method for impregnating a porous granule with an organic material which is at least partially immiscible with water, and sealing the material within the pores of the granule by covering the openings of the pores with a porous polyurea membrane, which method comprises (a) applying to said granule an organic solution comprising the material to be entrapped and an organic polyisocyanate, and (b) applying to the granule an aqueous solution comprising water and a catalytic amount of a catalyst selected from the group consisting of a basic organic tertiary amine and an alkyl tin carboxylate.

In another aspect, this invention relates to the impregnated granule produced by the above method.

The method and product of the present invention are characterized by the fact that the polyurea membrane is formed in situ at the interface between the two liquid phases. According to this invention, the reactant moieties are placed in contact only at the actual location where the membrane is formed. This procedure differs from prior art techniques of coating granules whereby all ingredients required for formation of the coating are first mixed together in a common body of fluid which is then applied to the granule in a single application.

According to the present invention, the organic solution is applied to the granule separately from and prior to the application of the aqueous solution. After the first application, at least some of the pores will contain liquid pools in which the polyisocyanate is dissolved. Although some dissolved polyisocyanate will inevitably settle on the outer granule surface, the amount of the latter will be negligible compared to the quantity in the pores. When the aqueous solution is applied, a liquid-liquid interface then forms at the pore opening, or at some level of depth inside the pore depending on how much of the pore was filled with non-aqueous solution. At this interface the following reactions take place (the polyisocyanate is represented by the symbol —NCO):

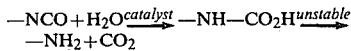
$$-NH_2 + CO_2$$

The rate determining step in the above sequence is the reaction between the polyisocyanate and water to form the carbamic acid. The slowness of this reaction is partially due to the fact that the polyisocyanate and water are located in separate phases. Furthermore, once the membrane starts to form, water molecules must diffuse through it to reach the polyisocyanate molecules. The reaction rate is thus slowed down even further.

Once the carbamic acid is formed, however, its subsequent decomposition to the amine and $CO_2$ as shown above occurs instantaneously. Isocyanate groups located near the interface are thus converted to amino groups with two active hydrogens. These newly formed amino groups then proceed to react with unreacted isocyanates remaining in the organic phase to form polyureas according to the following reaction:

Like the carbamic acid decomposition, the above reaction occurs instantaneously, before the amines have a chance to diffuse away from the vicinity of the interface. The resulting polyurea membrane is thus formed at the interface.

The above reactions deplete the interfacial area of isocyanates, thus encouraging the diffusion of additional isocyanates from the bulk organic phase toward the interface. The polyurea membrane is thus formed at the interface itself and is highly uniform along the interfacial surface by virtue of drawing its components from the bulk of each phase. The material whose slow release is sought is thus enclosed within the pores and escapes primarily by diffusion through the membrane.

DETAILED DESCRIPTION OF THE INVENTION

The granular material to be used in the process of the present invention may be any porous inert solid substance which is insoluble in any of the liquid materials used in the process. Granules formed by extrusion, agglomeration, or prilling are useful in the present invention as well as materials in their naturally occurring form. Naturally occurring porous granules can be subjected to physical modification prior to use, such as drying, crushing, and screening, to achieve the desired size and moisture characteristics. In general, the granule size can range from under 1 millimeter to over 1 centimeter in diameter or length. In agricultural usage, a typical granule size is about 1 to 2 millimeters in diameter. Examples of such carriers are vermiculite, sintered clay granules, kaolin, attapulgite clay, sawdust, and granular carbon. A common commercially available carrier material is "Trusorb." This naturally occurring material comprises calcined claysericite granules, commonly of −24+48 mesh (Tyler) grain size, and has a typical chemical analysis as follows:

|  | Percent |
| --- | --- |
| Silica (SiO) | 85.40 |
| Aluminum oxide (A1O) | 4.48 |
| Iron oxide (FeO) | 0.88 |
| Calcium oxide (CaO) | 0.20 |
| Magnesium oxide (MgO) | 0.54 |
| Sodium and potassium oxide (RO) | 0.15 |
| Loss on ignition (largely combined water) | 8.35 |
|  | 100.00 |

The solution comprising the liquid to be retained in the pores and the polyisocyanate can be applied to the granule by any conventional technique. Spraying is the most common technique. Best results are achieved when all components of the solution are fully dissolved to render a single homogenous liquid phase. This can be achieved by selecting a polyisocyanate which is fully soluble in the liquid to be contained, or by limiting the concentration of either the liquid itself or the polyisocyanate in order that a fully homogeneous solution results. Homogeneity can also be accomplished by dissolving both the liquid to be contained and the polyisocyanate in a third component serving as a solvent. Any inert solvent which will form a separate phase on contact with water will be suitable, particularly aliphatic compounds, aromatic compounds, or their halogenated derivatives. Examples of solvents useful for this purpose include heptane, octane, benzene, toluene, xylene, mesitylene, methylene chloride, 1,2-dichloroethane, and chlorobenzene.

It is essential that the first solution form a separate phase when placed in contact with water. In many cases, the material to be contained is a biologically active material with a slight solubility in water. It is frequently this slight solubility in water which renders possible the diffusion of the material through the polyurea membrane, particularly when the surrounding medium is water itself or some material with a high water content, such as wet soil. The two-phase liquid system required for the present invention can be easily achieved with such a material by using a concentration in excess of that required for saturation of the aqueous solution. Thus, the process is particularly useful when it is used to control the release of liquids whose upper solubility limit in water is in the range of several hundred parts per million. Alternatively, an inert solvent may be used for the purpose of forming the second liquid phase, provided that the solvent is selected such that the material to be entrapped resides preferentially in the solvent.

A wide variety of liquids can be entrapped in the granule pores by the process of the present invention. The most useful liquids will be those which do not react with isocyanates, amines or water, or any of the catalysts contemplated for use in the present invention. Any non-reactive material which will diffuse through the polyurea membrane is thus suitable. The material may be a single chemical compound or a mixture of two or more compounds. The material may diffuse into water, soil, or any other surrounding medium.

Suitable chemical-biological agents to be entrapped include herbicides, insecticides, fungicides, hematocides, bactericides, rodenticides, molluscicides, acaricides, larvacides, animal, insect, and bird repellents, plant growth regulators, fertilizers, pheromones, sex lures and attractants, and flavor and odor compositions. Examples of herbicides include
S-propyl dipropylthiocarbamate,
α,α,α-trifluoro-2,6-dinitro-N,N-dipropyl-p-toluidine,
S-ethyl diisobutylthiocarbamate,
2,6-dichlorobenzonitrile,
1,1'-dimethyl-4,4'-bipyridinium dichloride,
2,4-dichlorophenoxy acetic acid,
sodium 2,4-dichlorophenoxy acetate,
ammonium 3-amino-2,5-dichlorobenzoate,
S-ethyl dipropylthiocarbamate,
S-ethyl hexahydro-1H-azepine-1-carbothioate,
S-ethyl cyclohexyl ethyl thiocarbamate,
2,4,5-trichlorophenoxyacetic acid,
2-methyl-4-chlorophenoxy acetic acid,
2,4-bis(3-methoxypropylamino)-6-methylthio-s-triazine,
2-chloro-4-ethylamino-6-isopropylamino-s-triazine,
2-ethylamino-4-isopropylamino-6-methylmercapto-s-triazine,
3-(3,4-dichlorophenyl)-1,1-dimethylurea,
N,N-diallyl-α-chloroacetamide,
N-(α-chloroacetyl)hexamethyleneimine,
N,N-diethyl-α-bromoacetamide, and
3-amino-2,5-dichlorobenzoic acid.
Examples of insecticides include
O-ethyl-S-phenylethyl phosphonodithioate,
S-(1,2-dicarbethoxyethyl)-O,O-dimethyl dithiophosphate,
methyl O,O-dimethyl-o,p-nitrophenyl phosphorothioate,
1,1,1-trichloro-2,2-bis(p-chlorophenyl), and
2,3-dihydro-2,2-dimethyl-7-benzofuranyl methyl carbamate,
Sex lures and attractants include methyl 4-allyl-2-methoxyphenol and tertiarybutyl 4-chloro-2-methyl cyclohexane carboxylate. For comprehensive lists of suitable pesticide compositions see O. Johnson, *Chemical Week*, pp. 39–64, June 21, 1972. Other compositions suitable for use in accordance with the invention will be known to those skilled in the art.

While there is no critical amount of non-aqueous solution to be applied to the granule, it will be apparent to one skilled in the art that once the pores are filled, further liquid will not be retained by the granule. Thus, the process of the invention is most efficiently operated with a quantity of non-aqueous solution approximately equal to or less than the available pore volume of the granules. The actual pore volume can be determined by oil absorptivity measurements or by such analytical techniques as nitrogen or mercury porosimetry. It is preferable that the pores be less than full after application of the non-aqueous solution, thereby allowing the subsequently applied aqueous solution to rest in the remaining pore volume. The two phases are thus held in contact more efficiently, resulting in improved uniformity of the membrane formed at the interface.

The term "polyisocyanate" is intended to include any organic molecule containing two or more isocyanate (—N≡C≡O) groups. When three or more such groups or two groups plus a third reactive group are present on one molecule, cross-linking with other polyfunctional groups can occur. The resulting membrane is of particularly sturdy structure.

Organic polyisocyanates which can be used in the present invention include conventional aliphatic, alicyclic, and aromatic polyisocyanates. Aromatic polyisocyanates are preferred. Examples of suitable polyisocyanates are:
hexamethylene-1,6-diisocyanate
1-chloro-2,4-phenylene diisocyanate
m-phenylene diisocyanate
p-phenylene diisocyanate
4,4'-methylene-bis(phenyl isocyanate)
2,4-toluene diisocyanate
2,6-toluene diisocyanate
3,3'-dimethyl-4,4'-biphenylene diisocyanate
4,4'-methylene bis(2-methylphenyl isocyanate)
3,3'-dimethoxy-4,4'-biphenylene diisocyanate
2,2',5,5'-tetramethyl-4,4'-biphenylene diisocyanate
1,5-naphthalene diisocyanate Polymeric isocyanates such as polymethylene polyphenylisocyanates can also be used such as those sold under the trade names "Mondur MRS ®" (Mobay Chemical Company) and "PAPI ®" (The Upjohn Company). Some of the above-mentioned polyisocyanates have shown particular efficacy when used in combinations of two or more. One such example is an 80:20 weight percent blend of the 2,4- and 2,6-isomers of toluene diisocyanate. Another such example is a 65:35 weight percent blend. These combinations are commercially available under trade names such as "Hylene TM ®" (E. I. Depont de Nemours & Co., Inc.), "Nacconate 80 ®" (Allied Chemical Corporation), and "Mondur TD-80 ®" (Mobay Chemical Company). Addition products of polyisocyanates and polyols to form isocyanate prepolymers are also suitable for use in the present invention. Examples include:
hexamethylene diisocyanate and hexanetriol
2,4-toluene diisocyanate and benzocatechol
2,4-toluene diisocyanate and hexanetriol
2,4-toluene diisocyanate and trimethylol propane xylylene diisocyanate and trimethylol propane A further listing of useful commercially available polyisocyanates is found in the *Encyclopedia of Chemical Technology*, Kirk and Othmer, Second Edition, Volume 12, Interscience Publishers (1967) at pages 46–47.

It will be apparent to one of ordinary skill in the art of polymeric encapsulation that the diffusion properties of the membrane will be determined by the membrane thickness. The thickness will be determined by such considerations as the desired rate of diffusion of the entrapped material through the membrane and general considerations of process economy. The concentration of organic polyisocyanate in the non-aqueous solution determines the membrane thickness. A wide range of polyisocyanate concentration can thus be used, subject only to the above considerations. Generally, however, it will be most convenient to use a polyisocyanate concentration of from about 2% to about 75% by weight. Preferably, the concentration will range from about 5% to about 50% by weight of the non-aqueous mixture.

In the second step of the process, an aqueous solution comprising water and a catalyst is applied to the granule to which the non-aqueous solution has already been applied. The same method of application used for the non-aqueous solution can be used to apply the aqueous solution. The quantity of aqueous solution added will be at least enough to fully cover all liquid surfaces of the non-aqueous solution previously applied. This result is most easily achieved when a sufficient quantity of aqueous solution is applied to cover the entire outer surface of the granule including all pore openings as well as bare externally exposed solid surfaces of the granule. It will be most convenient to apply an amount in excess of this quantity, particularly when the pores are less than completely filled with the non-aqueous phase. In the latter case, excess aqueous solution will be retained in the pore volume previously unfilled by the non-aqueous solution. Such a technique of application promotes fuller interfacial contact between the two liquid phases and a product which is easy to handle since all liquid will be situated inside the pores and none on the outer granule surface.

Catalysts suitable for use in the present invention are basic organic tertiary amines and alkyl tin carboxylates. Included among such amines are monoamines and polyamines, as well as amines containing further non-carbon atoms such as oxygen. Examples of tertiary amines useful in the present invention are
triethylamine
triethylenediamine
tri-n-butylamine
trimethylamine
N-methylmorpholine,
N,N,N-dimethylethanolamine
triethanolamine
N,N,N',N'-tetramethyl-1,3-butanediamine
N,N,N',N'-tetrakis-(2-hydroxypropylamine).
Examples of alkyl tin carboxylates which are useful as catalysts in the present invention are
dibutyltin diacetate
tributyltin acetate
dibutyltin dilaurate
dibutyltin laurate
dibutyltin maleate
dibutyltin laurate maleate
dibutyltin-bis(6-methylaminocaproate)

The amount of catalyst which will constitute a catalytic amount and thus be useful to the process of the invention will be apparent to one of ordinary skill in the art as any amount which increases the rate of reaction between water and the polyisocyanate. The extent of catalytic effect will vary with the particular isocyanate used, the concentration of the isocyanate in the non-aqueous phase, and the temperature of the solutions during the application process. More reactive polyisocyanates and higher temperatures will diminish the quantity of catalyst required. Thus, there is no critical range of catalyst concentration. Generally, however, it will be most convenient to use a catalyst concentration of between about 0.1% and about 10% by weight in the aqueous phase. Preferably, the catalyst concentration will range from about 0.05% to about 5% by weight.

As a variation on the basic process, the rate of reaction can be further enhanced by a phase transfer catalyst. By promoting contact between reactants located in separate phases, a phase transfer catalyst can enhance both the reaction between the polyisocyanate and water and the reaction between the polyisocyanate and its amine derivative. Typical known phase transfer catalysts can be used to achieve this result. Quaternary ammonium salts are example of such catalysts, particularly tricaprylylmethylammonium chloride (Aliquat ® 336) and dimethyldicocoammonium chloride (Aliquat ® 221), both products of General Mills Company, Chemical Division, Kankakee, Ill.

While the temperature at which the process of the present invention can be performed is not critical, it will be most convenient to apply the solutions at approximately ambient temperature, about 15° C. to about 30° C. In general, however, the rate of reaction can be increased with increasing temperature, and the upper temperature limit will be determined by such considerations as stability of the materials to be entrapped in the pores and loss of any of the liquid materials by vaporization. Temperatures close to room temperature are particularly preferred when toxic system components are used. Such toxic substances may be either the material to be entrapped or the polyisocyanate.

Upon completion of the coating process any excess liquid not absorbed by the granule pores can be removed by evaporation. Frequently, removal of excess liquid is not necessary, particularly when a quantity of non-aqueous phase less than that required to fill the pores was originally used. Excess unreacted aqueous phase will then be absorbed by the remaining pore volume, resulting in a coated granule ready for use and easy to handle without further treatment.

Specific examples are set forth below showing the preparation of coated granules according to the process and product of the present invention, and the resulting slow-release effects. These examples are included for illustrative purposes only, and are not intended to be interpreted as imposing any limitations on the scope of the invention. Such limitations are set forth in the appended claims.

EXAMPLES 1–11

Water Submersion Test

Examples 1–11 are offered to show the results of a water submersion test to demonstrate the slow-release properties of granules prepared according to the present invention. The materials used were Trusorb granules of −24+48 Tyler mesh size, the herbicide S-ethyl hexahydro-1H-azepine-1-carbothioate, and the polyisocyanate PAPI ® (a polymethylene polyphenylisocyanate, available from The Upjohn Co.).

To prepare the granules, a solution of the herbicide and PAPI ® at the indicated weight ratio was sprayed using compressed air and a spray nozzle onto Trusorb granules in a rotating drum. A phase transfer catalyst, when used, was added to the herbicide-PAPI ® mixture prior to the spraying. The phase transfer catalyst used was tricaprylylmethylammonium chloride, a product of General Mills Co., designated as ALIQUAT 336 ®. The quantity of solution sprayed onto the granule was such as to achieve approximately 10% by weight of herbicide in the final product.

After the first spray, a second spray was applied in the same manner, consisting of an aqueous solution of amine catalyst at a concentration of approximately 1% by weight, such that the amount of amine in the final product was about 0.1% by weight, excluding water.

Following the second spray, a small quantity of a wetting agent was added to the drum for the purpose of facilitating the dispersion of the coated granules in water during the water durability test. The wetting agent used was Aerosol OTB ®, a product of American Cyanamide Corp., identified as a dioctyl ester of N-sulphosuccinic acid.

Upon completion of the granule preparation a pretest value of the herbicide content was determined by weighing a sample of the coated granules and extracting the herbicide therefrom by refluxing the sample in a 60:40 volume ratio mixture of chloroform and acetone for one hour. The herbicide content of the mixture was then determined by a gas chromatographic analysis using a flame photometric detector.

For the submersion test, a quantity of 100 milligrams of the coated granules was placed in two liters of water for a period of 48 hours. The granules were then filtered from the water and evaluated for herbicide content in the same manner as indicated above. The resulting value was then divided by the initial value to give the figure listed in Table I. The first entry in the Table represents an uncoated granule impregnated with the herbicide only. Comparison with the remainder of the results shows a large and consistent increase in herbicide retention in the granules.

TABLE I

Water Submersion Test Results After 48 Hours

Herbicide: S-ethyl hexahydro-1H-azepine-1-carbothioate, designated as AI (active ingredient)
Polyisocyanate: PAPI ®
Granule: Trusorb

| Example Number | Weight Ratio AI:PAPI | Catalyst | Percent AI Remaining |
|---|---|---|---|
| 1 (control) | 1:0 | — | 0.3 |
| 2 | 1:1 | TEA[a] | 21 |
| 3 | 1:0.25 | TEA, 336[b] | 1.0 |
| 4 | 1:0.5 | TEA, 336 | 8.0 |
| 5 | 1:1 | TEDA[c] | 18.1 |
| 6 | 1:0.5 | TEA | 7.0 |
| 7 | 1:0.5 | TEA | 6.0 |
| 8 | 1:1 | TEA, 336 | 15.5 |
| 9 | 1:1 | TEA, 336 | 17.5 |
| 10 | 1:1 | TEA | 20.8 |
| 11 | 1:1 | TEA, 336 | 9.5 |

[a]TEA:triethylamine
[b]336:ALIQUAT 336 ®200
[c]TEDA:triethylenediamine

EXAMPLES 12–14

Greenhouse Test on Paddy Rice

Examples 12–14 are offered to show the effectiveness of the slow-release properties of the coated granules in controlling weeds present in rice paddies. The granules were prepared in the same manner and from the same materials as those described above. The test was conducted as follows:

Plastic tubs measuring 10×7.5×5.75 inches (25.4×19.0×14.6 centimeters) were filled to a depth of 2 inches (5.1 centimeters) with 8 pounds (3.6 kilograms) of a loamy sand soil, containing 50 parts per million (ppm) each of cis-N[(trichloromethyl)thiol]-4-cyclohexene-1,2-dicarboximide (a commercial fungicide designated as "Captan ®") and 18-18-18 fertilizer (containing 18% N, 18% $P_2O_5$, and 18% $K_2O$ on a weight basis). One pint (0.47 liter) of the soil was removed, the remaining soil was leveled and seven rows were impressed across the width of the flat. Yellow nutsedge tubers (Cyperus esculentus), and rice (Oryza sativa) were planted in separate rows. The pint of soil was then used to place a 0.5 inch (1.27 centimeter) layer over the seeds and tubers. The planted soil was placed in a greenhouse, and irrigated by sprinkling as needed to keep the soil moist. Three days after the initial seeding another rows was impressed 0.5 inches (1.27 centimeters) deep across the width of the flat and seeds of watergrass (Echinochloa crusgalli) were planted and covered by pinching together the soil on either side of the seeder row. Seven to ten days after the original seeding, the soil was flooded with 2 inches (5.1 centimeters) of water. At flooding time the grass species were in the two leaf stage 1 to 2 inches (2.54 to 5.1 centimeters) high and the nutsedge was 1 inch (2.54 centimeters) high. The prepared granules were then added to the flooded soil in such quantity as to achieve an equivalent application rate of 0.75 pounds active ingredient (herbicide) per acre (lb/A) (0.84 kilogram/hectare). For three weeks after the granule application, the tubs were allowed to stand and water was added as needed to maintain the water level. At the end of three weeks, the species were rated visually as percent control from 0 to 100%, where 0% represents no injury and 100% represents complete kill when compared to the untreated check. The percent control was based on the total injury to the plants due to all factors.

The results in terms of percent control are listed in Table II, in which the first entry represents an uncoated granule impregnated with herbicide only. As in the previous examples, comparison of the uncoated and coated granules shows a large and consistent improvement in herbicide effectiveness owing to the retention characteristics of the coating.

TABLE II

Greenhouse Test Results After Three Weeks at 0.75 lb/A

Herbicide: S-ethyl hexahydro-1H-azepine-1-carbothioate, designated as AI (active ingredient)
Polyisocyanate: PAPI ®
Granule: Trusorb

| Example Number | Weight Ratio AI: PAPI ® | Catalyst | Percent Control |
|---|---|---|---|
| 12 | 1:0 | — | 20 |
| 13 | 1:1 | TEA[a] | 80 |
| 14 | 1:0.5 | TEA | 60 |

[a]TEA: triethylamine

EXAMPLES 15–20

Air Volatility Test

Examples 15–20 are offered to demonstrate how the present invention affects the release rate of volatile liquids into the atmosphere from granule pores. The granular material and the polyisocyanate used in these tests were the same as those used in Examples 1–14. The liquid retained in the granule pores (the active ingredient) was S-ethyl di-n-propylthiocarbamate (Examples 15–17), S-n-propyl di-n-propylthiocarbamate (Examples 18–19) and S-ethyl diisobutylthiocarbamate (Example 20).

The granules were prepared and a pre-test value of the active ingredient content was determined in the manner described in Examples 1–11. For each experiment, 100 milligram samples of both coated and uncoated granules, the latter included for comparison, were placed in a vented oven at 50° C. for 2 hours. The samples were then removed from the oven and analyzed for their thiocarbamate content by the technique described in Examples 1–11, involving refluxing the granules in a chloroform-acetone mixture and performing a gas chromatography analysis on the resulting solution.

The test results are listed in Table III. Variations in the quantity retained in the uncoated granule from one example to the next reflect variations in the oven conditions. The results pertaining to coated and uncoated granules in any single example, however, were obtained under identical conditions, representing samples run side by side at the same time. Each example shows a significant improvement in the coated granule over its uncoated counterpart, by demonstrating a substantial increase in the percentage of the original quantity of active ingredient retained in the granules after 2 hours.

TABLE III

Air Volatility Test Results After 2 Hours

Active Ingredient(AI):
Examples 15–17: S-ethyl di-n-propylthiocarbamate
Examples 18–19: S-n-propyl di-n-propylthiocarbamate
Examples 20 : S-ethyl diisobutylthiocarbamate
Polyisocyanate: PAPI ®
Granule: Trusorb

| Example Number | Weight Ratio AI:PAPI | Catalyst | Percent AI Remaining Uncoated | Coated |
|---|---|---|---|---|
| 15 | 2:1 | TEA[a] | 14.9 | 22.8 |
| 16 | 2:1 | TEA | 12.7 | 38.0 |
| 17 | 2:1 | TEA | 12.7 | 40.0 |
| 18 | 2:1 | TEA | 28.4 | 37.6 |
| 19 | 2:1 | TEA | 40.7 | 75.1 |
| 20 | 2:1 | TEA | 14.4 | 48.4 |

[a]Triethylamine

What is claimed is:

1. A method for impregnating a porous granule with a material which is at least partially immiscible with water and sealing said material within the pores of said granule by covering the openings of said pores with a porous membrane to effect a slow rate of release of said material from said granule, which comprises
   (a) applying to said granule an organic solution comprising said material and an organic polyisocyanate, and
   (b) applying to said granule an aqueous solution comprising water and a catalytic amount of a catalyst selected from the group consisting of a basic organic tertiary amine and an alkyl tin carboxylate.

2. A method according to claim 1 in which said organic polyisocyanate is an aromatic polyisocyanate.

3. A method according to claim 1 in which said organic polyisocyanate is a polymethylene polyphenylisocyanate.

4. A method according to claim 1 in which the concentration of organic polyisocyanate in said organic solution is within the range of about 2% to about 75% by weight.

5. A method according to claim 1 in which the concentration of said organic polyisocyanate in said organic solution is within the range of about 5% to about 50% by weight.

6. A method according to claim 1 in which the concentration of said catalyst in said aqueous solution is within the range of about 0.01% to about 10% by weight.

7. A method according to claim 1 in which the concentration of said catalyst in said aqueous solution is within the range of about 0.05% to about 5% by weight.

8. A method according to claim 1 in which said organic and aqueous solutions are applied at a temperature within the range of about 15° C. to about 30° C.

9. A method according to claim 1 in which said material sealed within said pores is S-ethyl hexahydro-1H-azepine-1-carbothioate.

10. A method according to claim 1 in which said material sealed within said pores is S-ethyl diisobutyl thiocarbamate.

11. A method according to claim 1 in which said material sealed within said pores is S-propyl dipropylthiocarbamate.

12. A method according to claim 1 in which said material sealed within said pores is S-ethyl dipropylthiocarbamate.

13. A method according to claim 1 in which said material sealed within said pores is O-ethyl S-phenyl ethylphosphonodithioate.

14. A method according to claim 1 in which said material sealed within said pores is S-ethyl cyclohexylethylthiocarbamate.

15. An article of manufacture which comprises a porous granule impregnated with a material which is at least partially immiscible with water, the pores of which are sealed with a porous polyurea membrane formed by
   (a) applying to said granule an organic solution comprising said material and an organic polyisocyanate, and
   (b) applying to said granule an aqueous solution comprising water and a catalytic amount of a catalyst selected from the group consisting of a basic organic tertiary amine and an alkyl tin carboxylate.

16. An article of manufacture according to claim 15 in which said organic polyisocyanate is an aromatic polyisocyanate.

17. An article of manufacture according to claim 15 in which said organic polyisocyanate is a polymethylene polyphenylisocyanate.

18. An article of manufacture according to claim 15 in which the concentration of said organic polyisocyanate in said organic solution is within the range of about 2% to about 75% by weight.

19. An article of manufacture according to claim 15 in which the concentration of said organic polyisocyanate in said organic solution is within the range of about 5% to about 50% by weight.

20. An article of manufacture according to claim 15 in which the concentration of said catalyst in said aqueous solution is within the range of about 0.01% to about 10% by weight.

21. An article of manufacture according to claim 15 in which the concentration of said catalyst in said aqueous solution is within the range of about 0.05% to about 5% by weight.

22. An article of manufacture according to claim 15 in which said organic and aqueous solutions are applied at a temperature within the range of about 15° C. to about 30° C.

23. An article of manufacture according to claim 15 in which said material sealed within said pores is S-ethyl hexahydro-1H-azepine-1-carbothioate.

24. An article of manufacture according to claim 15 in which said material sealed within said pores is S-ethyl diisobutylthiocarbamate.

25. An article of manufacture according to claim 15 in which said material sealed within said pores is S-propyl dipropylthiocarbamate.

26. An article of manufacture according to claim 15 in which said material sealed within said pores is S-ethyl dipropylthiocarbamate.

27. An article of manufacture according to claim 15 in which said material sealed within said pores is O-ethyl S-phenyl ethylphosphonodithioate.

28. An article of manufacture according to claim 15 in which said material sealed within said pores is S-ethyl cyclohexylethylthiocarbamate.

* * * * *